United States Patent [19]

Remy

[11] 4,220,651
[45] Sep. 2, 1980

[54] ANTIPSYCHOTIC LEVOROTATORY ENANTIOMERS OF 3-HALOCYPROHEPTADINES, ANALOGS AND DERIVATIVES

[75] Inventor: David C. Remy, North Wales, Pa.

[73] Assignee: Merck & Co., Inc., Rahway, N.J.

[21] Appl. No.: 40,819

[22] Filed: May 21, 1979

Related U.S. Application Data

[63] Continuation-in-part of Ser. No. 15,253, Feb. 26, 1979, abandoned, which is a continuation-in-part of Ser. No. 323, Jan. 2, 1979, abandoned.

[51] Int. Cl.² ............................................. A61K 31/445
[52] U.S. Cl. ..................................................... 424/267
[58] Field of Search ........................ 424/267; 546/203

[56] References Cited

U.S. PATENT DOCUMENTS

| 3,014,911 | 12/1961 | Engelhardt | 260/293 |
|---|---|---|---|
| 3,851,059 | 11/1974 | Prugh | 424/267 |
| 4,031,222 | 6/1977 | Remy | 424/267 |
| 4,031,223 | 6/1977 | Remy | 424/267 |

OTHER PUBLICATIONS

Engelhardt et al., J. Med. Chem. 8, p. 829–835 (1965).
Ebnöther et al., *Helv. Chem. Acta*, 48-1237-1249, (1965), Eng. Trans.

*Primary Examiner*—Stanley J. Friedman
*Attorney, Agent, or Firm*—William H. Nicholson; Mario A. Monaco

[57] ABSTRACT

The levorotatory enantiomers of 3-halocyproheptadines and related compounds are antipyschotic agents and certain members of the group are novel compounds. Their dextrorotatory counterparts find utility as a source for additional levorotatory enantiomer.

4 Claims, No Drawings

ANTIPSYCHOTIC LEVOROTATORY ENANTIOMERS OF 3-HALOCYPROHEPTADINES, ANALOGS AND DERIVATIVES

BACKGROUND OF THE INVENTION

This is a continuation-in-part of copending Application Ser. No. 15,253, filed Feb. 26, 1979, which in turn is a continuation-in-part of copending Application Ser. No. 323, filed Jan. 2, 1979 (both are now abandoned).

This invention is concerned with pharmaceutical compositions comprising levorotatory enantiomers of 3-halocyproheptadines and related compounds and their use as antipsychotic agents. It is also concerned with certain members of the group and their dextrorotatory counterparts which are novel compounds.

Racemic 3-bromocyproheptadine and 3-chlorocyproheptadine are disclosed in U.S. Pat. No. 3,014,911 as members of a large group of cyproheptadine derivatives which possess antiserotonin and antihistamine activity. They are also disclosed in *J. Med. Chem.*, 8, 829 (1965).

The levorotatory enantiomer of 3-chlorocyproheptadine is disclosed by Ebnöther et al., in *Helv. Chim. Acta,* 48(6), 1237–1249 (1965). The levorotatory enantiomer of 3-iodocyproheptadine is disclosed in U.S. Pat. No. 4,031,223 and the levorotatory enantiomer of 1-cyclopropylmethyl-4-(3-iodo-5H-dibenzo[a,d]cyclohepten-5-ylidene)piperidine is disclosed in U.S. Pat. No. 4,031,222.

Now with this invention there are provided novel pharmaceutical compositions comprising one or more of these levorotatory 3-halocyproheptadines and analogs thereof as active ingredient, which are useful as antipsychotic agents.

There is also provided a novel method of treating psychoses with these novel pharmaceutical compositions.

There are also provided certain novel compounds within the class of 3-halocyproheptadines and analogs thereof and novel processes for synthesizing these novel compounds.

DETAILED DESCRIPTION OF THE INVENTION

The novel compounds of this invention are the levorotatory and dextrorotatory enantiomers of the compound having the following structural formula:

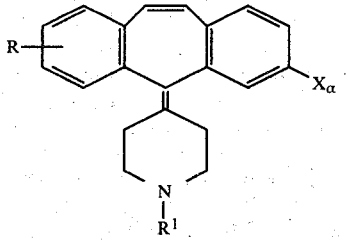

or pharmaceutically acceptable salts thereof, wherein $X_\alpha$ represents bromo or chloro; R represents hydrogen, lower alkyl, especially $C_{1-3}$ alkyl, or fluoro; $R^1$ represents methyl or cyclopropylmethyl, when $X_\alpha$ is bromo; and $R^1$ represents cyclopropylmethyl when $X_\alpha$ is chloro.

A preferred embodiment of the novel compounds is that wherein R is hydrogen.

An even more preferred embodiment of the novel compounds is that wherein R is hydrogen, and $X_\alpha$ is bromo.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, pamoate, citrate, napsylate, pyruvate, isethionate, maleate, fumarate, or the like.

The salts are prepared by dissolving approximately equimolecular amounts of the free base compound and the desired acid in a solvent followed by crystallization of the salt product.

The novel process for the preparation of the compounds of this invention comprises dehydration of an R-substituted 1-$R^1$-4-(3-$X_\alpha$-5-hydroxy-5H-dibenzo[a,d]cyclohepten-5-yl)piperidine with a dehydrating agent such as trifluoroacetic acid/trifluoroacetic anhydride at reflux temperature, as described in *J. Med. Chem.*, 8, 829 (1965), to form a racemic mixture of the novel compounds of this invention. The racemic mixture is then resolved by formation of diastereomeric salts with it and an optically active acid such as di-p-toluoyl-d-tartaric acid in a solvent such as ethanol followed by separation of the diastereomeric pair of salts such as by fractional crystallization followed by separate treatment of each salt with an alkali such as an alkali metal hydroxide, bicarbonate or carbonate, especially sodium bicarbonate or carbonate to liberate the free (+)- and (−)- enantiomers. The levorotatory isomer is further resolved via recrystallization from a solvent such as acetonitrile.

The optically enriched dextrorotatory compound obtained as described above can be racemized by heating a solution of it in an inert solvent until a sample fails to show optical activity. It is convenient to reflux a toluene solution for about 10–50 hours. In this manner, additional quantities of the racemic compound can be obtained from which additional levorotatory material can be isolated by the above described resolution.

The compounds useful in the novel method of treatment and novel pharmaceutical formulations of this invention have structural formula:

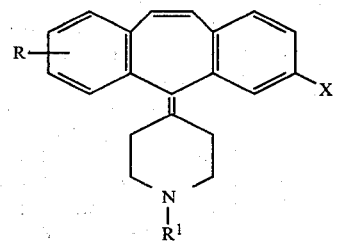

or a pharmaceutically acceptable salt thereof, wherein R is as previously defined; $R^1$ is methyl or cyclopropylmethyl; and X is halo, such as chloro, bromo, or iodo. It is preferred that R be hydrogen and X be bromo or iodo.

The pharmaceutically acceptable salts contemplated for this purpose are the same salts discussed herein in connection with the group of novel compounds.

As pointed out by Ebnöther et al., Helv. Chim. Acta, 48, 1237–1249 (1965) these compounds exist as levorotatory and dextrorotatory optical enantiomers. All of the antipsychotic activity resides in the levorotatory enantiomers, but the racemic mixtures of the levo- and dextrorotatory enantiomers, the mixture from which the levorotatory enantiomers are obtained are still potent antipsychotic agents and are useful in the novel method of treatment and novel pharmaceutical formulations of this invention. Thus there is contemplated for use in the novel method of treatment and pharmaceutical formulations:

(1) racemic mixtures of levo- and dextrorotatory enantiomers, herein after referred to as "racemic compounds"; and (2) any mixtures optically enriched in the levoratory sense or pure levoratotary enantiomers, hereinafter referred to as "levorotatory compounds".

The novel method of treatment of this invention comprises the administration of an antipsychotically effective amount of one of the racemic or levorotatory compounds or a pharmaceutically acceptable salt thereof to a psychotic patient. The route of administration can be oral, rectal, intravenous, intramuscular, or subcutaneous. Doses of 0.1 to 20 mg./kg./day and preferably of 0.5 to 10 mg./kg./day of active ingredient are adequate, and if preferred, it can be administered in divided doses given two to four times daily.

It is to be noted that the precise unit dosage form and dosage level depend upon the case history of the individual being treated and, consequently, are left to the discretion of the therapist.

Pharmaceutical compositions comprising a compound useful in the novel method of treatment as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg., and preferably from 5 to 250 mg.

EXAMPLE 1

(−)-1-Methyl-4-(3-bromo-5H-dibenzo[a,d]cyclohepten-5-ylidene)piperidine

Step A: Preparation of 1-methyl-4-(3-bromo-5-hydroxy-5H-dibenzo[a,d]cyclohepten-5-yl)-piperidine To an ice cooled solution of 2.10 g. (0.0074 mol) of 3-bromo-5H-dibenzo[a,d]cyclohepten-5-one in 35 ml. of dry tetrahydrofuran is added dropwise 36 ml. of 0.41 M 1-methyl-4-piperidylmagnesium chloride. The solution is stirred for one hour and then the tetrahydrofuran is removed by evaporation on a rotary evaporator. The red, oily residue that remains is dissolved in benzene and water is added dropwise until a clear benzene supernatant and a gelatinous aqueous phase is obtained. The benzene phase is decanted and the gelatinous aqueous phase is extracted with four 50 ml. portions of hot benzene. The combined benzene phases are washed with water, dried over magnesium sulfate, filtered, and benzene is removed on a rotary evaporator. The residue is triturated with cold acetonitrile and collected by filtration to give 0.86 g. (40%) of 1-methyl-4-(3-bromo-5-hydroxy-5H-dibenzo[a,d]cyclohepten-5-yl)piperidine.

Step B: Preparation of (±)-1-methyl-4-(3-bromo-5H-dibenzo[a,d]cyclohepten-5-ylidene)piperidine A solution of 0.86 g. (0.003 mol) of 1-methyl-4-(3-bromo-5-hydroxy-5H-dibenzo[a,d]cyclohepten-5-yl)piperidine in 30 ml. of trifluoroacetic acid and 15 ml. of trifluoroacetic anhydride is stirred and refluxed for 16 hours. The solvents are removed by evaporation on a rotary evaporator. The residue is dissolved in chloroform, and this chloroform solution is washed with sodium hydroxide solution, water, dried over magnesium sulfate, and filtered. Evaporation of the chloroform from the filtrate gives 0.88 g. of a yellow oil. This oil is dissolved in a minimum amount of absolute ethanol, treated with ethanolic HCl, and is cooled. The white crystalline material that precipitates is collected by filtration and is recrystallized from acetonitrile to give 0.67 g. of (±)-1-methyl-4-(3-bromo-5H-dibenzo[a,d]cyclohepten-5-ylidene)piperidine hydrochloride.

Step C: Preparation of (31)-1-methyl-4-(3-bromo-5H-dibenzo[a,d]cyclohepten-5-ylidene)piperidine To a solution of 12.42 g. (0.0339 mol) of (±)-1-methyl-4-(3-bromo-5H-dibenzo[a,d]cyclohepten-5-ylidene piperidine in 250 ml of hot ethanol is added 13.11 g. (0.0339 mol) of di-p-toluoyl-d-tartaric acid dissolved in 50 ml of warm ethanol. The solution is stirred and allowed to cool to room temperature. The salt that crystallizes is removed by filtration and is recrystallized from ethanol six times to afford 2.62 g. of material having a constant rotation: $[\alpha]_{589}^{25}$ −111°, $[\alpha]_{578}^{25}$ −116°, $[\alpha]_{546}^{25}$ −137°, $[\alpha]_{436}^{25}$ −306° (c, 0.531, pyridine). This salt is converted to the free base with saturated sodium bicarbonate solution and extracting it into ether. The ether phase is washed with water, dried over magnesium sulfate, filtered, and the ether is removed. Recrystallization from acetonitrile gives (−)-1-methyl-4-(3-bromo-5H-dibenzo[a,d]cyclohepten-5-ylidene)piperidine as TLC homogeneous (fl. alumina/CHCl₃), sparkling white prisms, m.p. 189°–190°; $[\alpha]_{589}^{25}$ −100°, $[\alpha]_{578}^{25}$ −106°, $[\alpha]_{546}^{25}$ −127°, $[\alpha]_{436}^{25}$ −304° (c, 0.731, CHCl₃).

Anal. Calcd. for $C_{21}H_{20}BrN$: C,68.86; H,5.50; Br,21,82; N,3.82. Found: C,68.97; H,5.58; Br,21.62; N,3.39.

EXAMPLE 2

(+)-1-Methyl-4-(3-bromo-5H-dibenzo[a,d]cyclohepten-5-ylidene)piperidine

Starting with 5.76 g (0.0157 mol) of (±)-1-methyl-4-(3-bromo-5H-dibenzo[a,d]cyclohepten-5-ylidene)-piperidine toluoyl-1-tartaric acid monohydrate in 25 ml. of ethanol and using the procedure as described above, 1.60 g of crystalline salt is obtained $[\alpha]_{589}^{25}$ +110°; $[\alpha]_{578}^{25}$ +116°; $[\alpha]_{546}^{25}$ +137°; $[\alpha]_{436}^{25}$ +302° (c, 0.403, pyridine). Conversion to the free base and crystallization from acetonitrile gives (+)-1-methyl-4-(3-bromo-5H-dibenzo[a,d]cyclohepten-5-ylidene)piperidine, m.p. 189°–191° C.; $[\alpha]_{589}^{25}$ +100°, $[\alpha]_{578}^{25}$ +107, $[\alpha]_{546}^{25}$ +127, $[\alpha]_{436}^{25}$ +307° (c, 0.651, CHCl₃).

Employing the procedures substantially as described in Examples 1 and 2 but substituting for the 3-bromo-5H-dibenzo[a,d]cyclohepten-5-one and/or the 1-methyl-4-piperidylmagnesium chloride used in Example 1, Step A similar relative amounts of the 3-$X_\alpha$-7-R-5H-dibenzo[a,d]-cyclohepten-5-ones, and 1-$R^1$-4-piperidylmagnesium chloride, described in Table I, there are produced the (−)- and (+)-enantiomers of 1-R[1]-4-(3-X$_a$-7-R-5H-dibenzo[a,d]-cyclohepten-5-ylidene)piperidine, also described in Table I in accordance with the following reaction scheme:

TABLE I

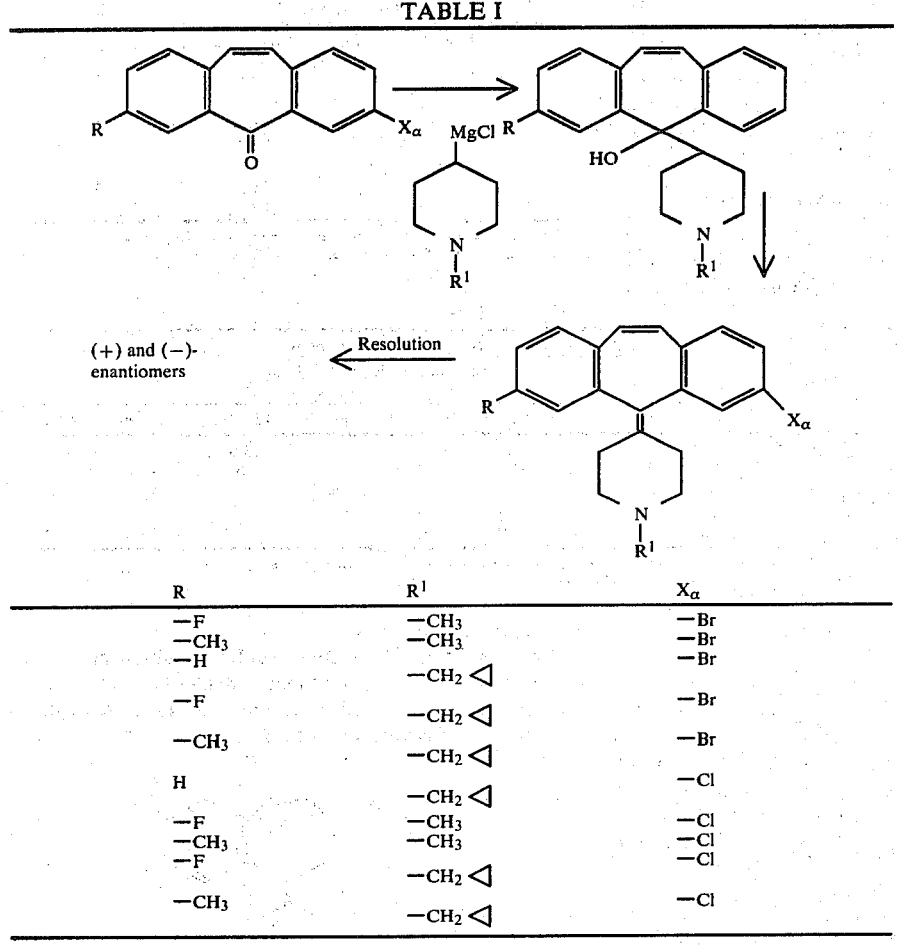

| R | R[1] | X$_a$ |
|---|---|---|
| —F | —CH$_3$ | —Br |
| —CH$_3$ | —CH$_3$ | —Br |
| —H | —Br | |
| | —CH$_2$◁ | |
| —F | —CH$_2$◁ | —Br |
| —CH$_3$ | —CH$_2$◁ | —Br |
| H | —CH$_2$◁ | —Cl |
| —F | —CH$_3$ | —Cl |
| —CH$_3$ | —CH$_3$ | —Cl |
| —F | —CH$_2$◁ | —Cl |
| —CH$_3$ | —CH$_2$◁ | —Cl |

EXAMPLE 3

Pharmaceutical Compositions

A typical tablet containing 100 mg. of (−)-1-methyl-4-(3-bromo-5H-dibenzo[a,d]cyclohepten-5-ylidene)-piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture is then compressed into tablets.

| Tablet Formula | |
|---|---|
| Ingredient | Mg. per Tablet |
| (-)-1-methyl-4-(3-bromo-5H-dibenzo[a,d]-cyclohepten-5-ylidene)piperidine | 100 mg. |
| Calcium phosphate | 52 mg. |
| Lactose | 60 mg. |
| Starch | 10 mg. |
| Magnesium stearate | 1 mg. |

Similarly tablets containing the other racemic or levorotatory compounds active in the novel method of treatment of this invention are prepared by substituting for the 100 mg (2.7×10$^{-4}$ mole) of (−)-1-methyl-4-(3-bromo-5H-dibenzo[a,d]cyclohepten-5-ylidene)piperidine a comparable molecular amount of any of the racemic or levorotatory compounds with structural formula:

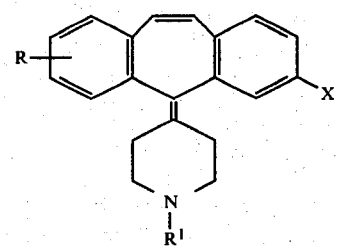

or a pharmaceutically acceptable salt thereof wherein X, R and R[1] are as previously defined.

Pharmacology

I. Antagonism of (+)-Amphetamine

Methods:

Mice (CF$_1$ females weighing about 20 g.) were injected i.p. with the test compounds two hours and five minutes prior to a subcutaneous administration of (+)-amphetamine, 10 mg./kg. Forty-five minutes after giving (+)-amphetamine, the mice were observed for the presence or absence of excitement and locomotor stimulation elicited by (+)-amphetamine.

Results:

At a dose of 30 mg./kg. of (−)-1-methyl-4-(3-iodo-5H-dibenzo[a,d]cyclohepten-5-yldiene)-piperidine (L-634,340) or (−)-1-methyl-4-(3-bromo-5-H-dibenzo[a,d]cyclohepten-5-ylidene)piperidine (L-636,524), 80% of the mice failed to exhibit the typical signs normally elicited by (+)-amphetamine. A reference neuroleptic, chlorpromazine, also antagonized the action of (+)-amphetamine (Table 1).

II. Antiavoidance Activity in Squirrel Monkeys

Methods:

Squirrel monkeys (*Saimiri sciureus*) of both sexes were trained to press a lever in order to avoid an electric shock. The animals were trained and tested while restrained in a chair in an isolation chamber. The electric shock (600 V a.c., 2 mA, 1 second) was given via leads placed on the seat of the chair and a ring around the animal's neck. Background noise was supplied with a Grason Stadler Noise Generator. A modified Sidman avoidance schedule (RS-36, SS-36) was used, programming 36 seconds of shock-free time after each lever press (avoidance response). A lever press made during a shock (escape response) immediately terminated the shock, resetting the shock-shock interval timer to 36 seconds. The avoidance schedule also contained an "alarm" system to shut off the schedule for 30 minutes, if an animal received 10 consecutive shocks without a lever press. This prevented the animals from receiving an excessive number of shocks. Following the 30-minute alarm period, the schedule resumed again. An animal was assigned the maximum number of shocks (50/30 minutes), if the alarm system was activated during a trial. The test compounds were administered by gavage at cumulative doses of 0.33, 1 and 3 mg./kg. given at 0, 90 and 180 minutes of the test session.

Results:

(−)-1-methyl-4-(3-iodo-5H-dibenzo[a,d]cyclohepten-5-ylidene)piperidine (L-634,340) caused the monkeys to take a large number of shocks, i.e. avoidance responding was markedly depressed (Table 2). Chlorpromazine, a reference standard, also exhibits a similar action in this test procedure.

Table 1

| Antagonism of (+)-amphetamine-induced excitement and hyperactivity. | | |
|---|---|---|
| Treatment[a] (mg./kg. i.p.) | | #Protected[b] #Tested |
| L-634,340-OOP-02 | (6) | 2/5 |
| " | (30) | 4/5 |
| " | (150) | 5/5 |
| L-636,524-OOY-01 | (6) | 0/5 |
| " | (30) | 4/5 |
| " | (150) | 5/5 |
| Chlorpromazine | (6) | 5/5 |
| " | (30) | 5/5 |
| " | (150) | |

[a]Two hours and five minutes before (+)-amphetamine (10 mg./kg. s.c.).
[b]Mice were observed 45 minutes after (+)-amphetamine.

Table 2

| | Antiavoidance activity in squirrel monkey. | | | | | | | | |
|---|---|---|---|---|---|---|---|---|---|
| | Shocks Received/30 Minutes Time (minutes) | | | | | | | | |
| Treatment | 0–30 | 30–60 | 60–90 | 90–120 | 120–150 | 150–180 | 180–210 | 210–240 | 240–270 |
| mg./kg. p.o.: | 0.33 | | | 1.0 | | | 3.0 | | |
| Control[a] | 0 | 0 | 0 | 1 | 0 | 0 | 0 | 0 | 0 |
| L-634,340[b] | 0 | 1 | 10 | 20 | 38 | 50 | 50 | 50 | 50 |
| Control[a] | 0 | 1 | 3 | 3 | 3 | 1 | 1 | 2 | 3 |
| Chlorpromazine[b] | 0 | 0 | 0 | 0 | 2 | 2 | 5 | 50 | 50 |

[a]Average of two control sessions (one before and one after drug testing) for three monkeys.
[b]Average for the same three monkeys for one session.

What is claimed is:

1. A method of treating psychoses which comprises the administration to a patient in need of such treatment an effective antipsychotic amount of a racemic or levorotatory compound of formula:

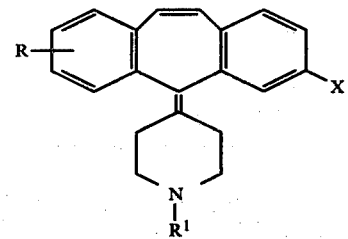

or pharmaceutically acceptable salt thereof wherein R is hydrogen, fluoro, or lower alkyl; $R^1$ is methyl or cyclopropylmethyl; and X is chloro, bromo, or iodo.

2. The method of claim 1, wherein R is hydrogen and X is bromo or iodo.

3. The method of claim 2 wherein the racemic or levorotatory compound is 1-methyl-4-(3-bromo-5H-dibenzo[a,d]cyclohepten-5-ylidene)piperidine or pharmaceutically acceptable salt thereof.

4. The method of claim 2 wherein the racemic or levorotatory compound is 1-cyclopropylmethyl-4-(3-iodo-5H-dibenzo[a,d]cyclohepten-5-ylidene)piperidine or a pharmaceutically acceptable salt thereof.

* * * * *